United States Patent [19]
Ober et al.

[11] Patent Number: 6,152,564
[45] Date of Patent: Nov. 28, 2000

[54] INFRARED EYE MOVEMENT MEASUREMENT DEVICE

[75] Inventors: Jan Krzysztof Ober; Jan Jakub Ober, both of Poznan, Poland

[73] Assignees: Bertec Corporation, Worthington, Ohio; Ober Consulting LTD, Poland

[21] Appl. No.: 09/455,261

[22] Filed: Dec. 6, 1999

[51] Int. Cl.[7] ........................................................ A61B 3/10
[52] U.S. Cl. ............................................................ 351/210
[58] Field of Search ..................................... 351/205, 209, 351/210, 245, 221, 158; 600/558, 595

[56] References Cited

U.S. PATENT DOCUMENTS 4,102,564  7/1978  Michael ................................. 351/210

*Primary Examiner*—George Manuel
*Attorney, Agent, or Firm*—Francis T. Kremblas, Jr.

[57] ABSTRACT

Disclosed herein is a device for measuring horizontal and vertical eye movement utilizing infrared technology. The device rests on the user's nose and, in alternate versions, can be secured to the user's head via a head strap or temple arms which will provide greater alignment and applications. It is comprised of a nose bridge piece and mounting means which house the calculation and measurement technology. The nose bridge is similar to that of ordinary eye glasses with the mounting means, or head strap, or temple arms attached thereto. The mounting means consist of a light-weight horizontal component which extends from the nose bridge and underneath the eyes. This component is located below the horizontal center of the eye and rests above the cheek area of the user's face. Illuminators, which are oriented approximately linear to the horizontal axis of the eye on the component, radiate light into the lower portion of the eye. Sensors, which are above and below the illuminators on the component, detect and measure the amount of reflected light. The device is capable of measuring both axes independently and jointly, as well as both eyes independently and jointly. Utilizing a robust algorithm, accurate adjustment and alignment are not required. The device itself does not require adjustment or alignment, only adjustments for the user's facial features are needed. Therefore, this device only obstructs the bottom portion of the user's lower field of view, leaving the forward, side-to-side, and upward fields completely unobstructed, as well as requires only minimal adjustment and alignment. Thus, it has advantages, applications, and usefulness not contemplated by the prior art.

1 Claim, 3 Drawing Sheets

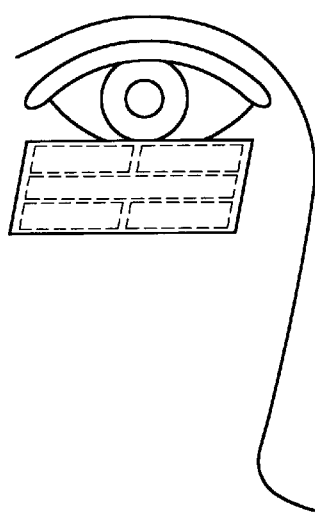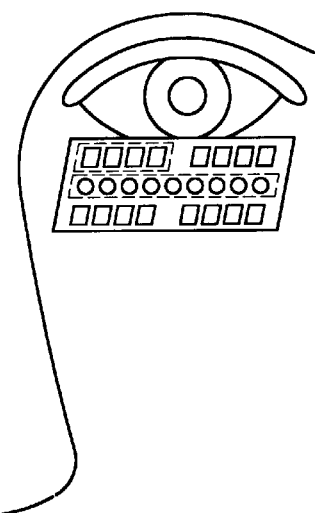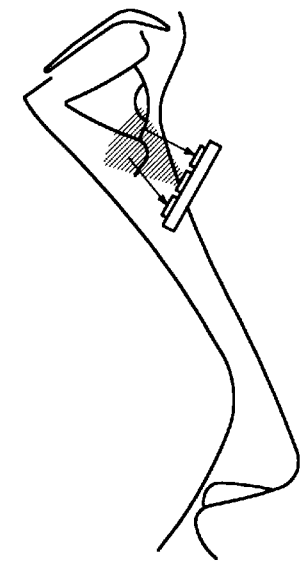
FIG-1A    FIG-1B

INFRARED EYE MOVEMENT MEASUREMENT DEVICE

BACKGROUND OF THE INVENTION

The presently disclosed device relates to the measurement of eye movement. Regarding eye movement measurement devices, the prior art required precise adjustments for each subject, and complete to partial blocking of the subject's visual range which detrimentally inhibited testing capabilities. Certain devices limited the subject's mobility by requiring the subject to remain perfectly still during measurement. These prior devices were designed to be worn as goggles, helmets, or spectacles which housed the measurement technology.

The main types of eye movement measurement and monitoring systems in common use are: Infrared; Video; Electro-oculography; Limbus trackers; Purkinje reflection trackers, and Scleral Coil trackers. Limbus trackers are usually cheap and easy to use but generally these are only useful for measurements in one axis at a time, that is, they are not gaze monitors. For accurately assessing point of gaze the most common method is the video tracker, where the pupil or iris is imaged using a video camera and a simple image processing module extracts point of gaze, pupil diameter, and in some advanced systems ocular torsion all in real time. The disadvantage of video is that generally the sampling rate is restricted to the video frame rate, making such systems less suitable for looking at parameters such as saccadic latency. Purkinje reflection trackers may also be used as gaze monitors and have a high degree of accuracy and good temporal resolution but are very difficult to set up. Finally, Scleral coil systems, in which a small coil is placed on a contact lens and its position measured within a large frame bounded by other coils, allow measurement of point of gaze and ocular torsion at high spatial and temporal resolutions. However, Scleral coils are invasive, such that a hard annular contact lens must be attached directly to the eye, which typically has a maximum wearing time of 30 minutes.

The present invention overcomes the shortcomings of the prior art by requiring minimal adjustment for accurate measurement of horizontal and vertical eye movement utilizing direct infrared illuminators and sensors, only minimally obstructing the lower portion of the user's visual range, being made of low cost and readily available material, and by being comprised of a comfortable and efficient design of an adjustable nose bridge with the measuring and calculation means attached thereto. The presently disclosed device requires only a minimal aperture or frame, and, does not require any additional optics such as, lenses, mirrors, or prisms as did the prior art.

BRIEF SUMMARY OF THE INVENTION:

The purpose of the disclosed invention is to provide the means for measuring horizontal and vertical eye movement. The present invention is directed to an eye movement measurement device that satisfies the adjustment, alignment, comfort, measurement, and view obstruction needs identified in the BACKGROUND section above.

This object is accomplished by disclosing an eye movement measurement device, and versions thereof, capable of measuring the horizontal and vertical movement(s) of one eye independently, or measuring both eyes jointly, as well as being capable of measuring both axes independently and jointly. The device is placed on the user's nose and employs robust algorithms to compensate for minor misplacement, thereby only requiring minimal adjustment or alignment for accurate measurement. The nose bridge piece obstructs no more of the user's view than the user's nose. The horizontal component of the mounting means, which is attached to the nose bridge piece and houses the calculation and measurement means, only obstructs the bottom portion of the user's lower field of view by resting below the eye at approximately cheek level. The horizontal component(s) extend from the nose bridge under the center of the eye(s) and rests between the lower eye and cheek area of the user's face. Thus, the user's forward, side-to-side, and upward views are totally unobstructed by the device.

The preferred embodiment of the device utilizes infrared measurement means. The infrared illuminators are attached to the horizontal component of the mounting means and oriented along the horizontal axis of the eye(s) in an approximately linear fashion. The sensors (e.g. photo detectors) are located above and below the illuminators. Therefore, the full range of horizontal and vertical eye movement can be measured with minimal inconvenience to the application and minimal view obstruction.

A head strap or temple arms may be added to provide secure attachment to the user's head, thus increasing the device's applicability and usefulness.

Therefore, the disclosed device is capable of measuring horizontal and vertical eye movement independently and jointly, as well as measuring both eyes independently and jointly. It provides a wide range of applications, tests, and uses via its simplicity of design by only requiring minimal adjustment and alignment, and causing only minimal view obstruction.

BRIEF DESCRIPTION OF THE SEVERAL VIEWS OF THE DRAWINGS

FIG. 1A is a front view of the preferred location and orientation of the horizontal component(s) of the mounting means, and the illuminators and sensors of the measuring means. The illuminating and sensing means face the user's eye(s).

FIG. 1B is a side view of the mounting means and measuring means with the shaded cone indicating illumination and the arrows indicating light reflection.

FIGS. 1A and 1B are for the Official Gazette.

FIG. 3A shows the eye looking upward.

FIG. 3B shows the eye looking forward.

FIG. 3C shows the eye looking downward.

FIG. 4 shows off axis and horizontal eye movement measurement. The lighter shading indicates the sensor(s) receiving more light reflection when the eye's corneal bulge moves closer to the sensor(s).

DETAILED DESCRIPTION OF THE INVENTION

A. Preferred Embodiments

The invention disclosed herein relates to an eye movement measurement device which utilizes infrared technology to measure horizontal and vertical eye movement, capable of measuring each eye independently or both eyes jointly, and measuring horizontal and vertical movements separately or jointly.

The device is comprised of a nose bridge and mounting means. The nose bridge is similar in design to that used on ordinary eye glasses and rests on the user's nose. The mounting means are attached to the nose bridge and house the measuring and calculation technology.

Figure 2:
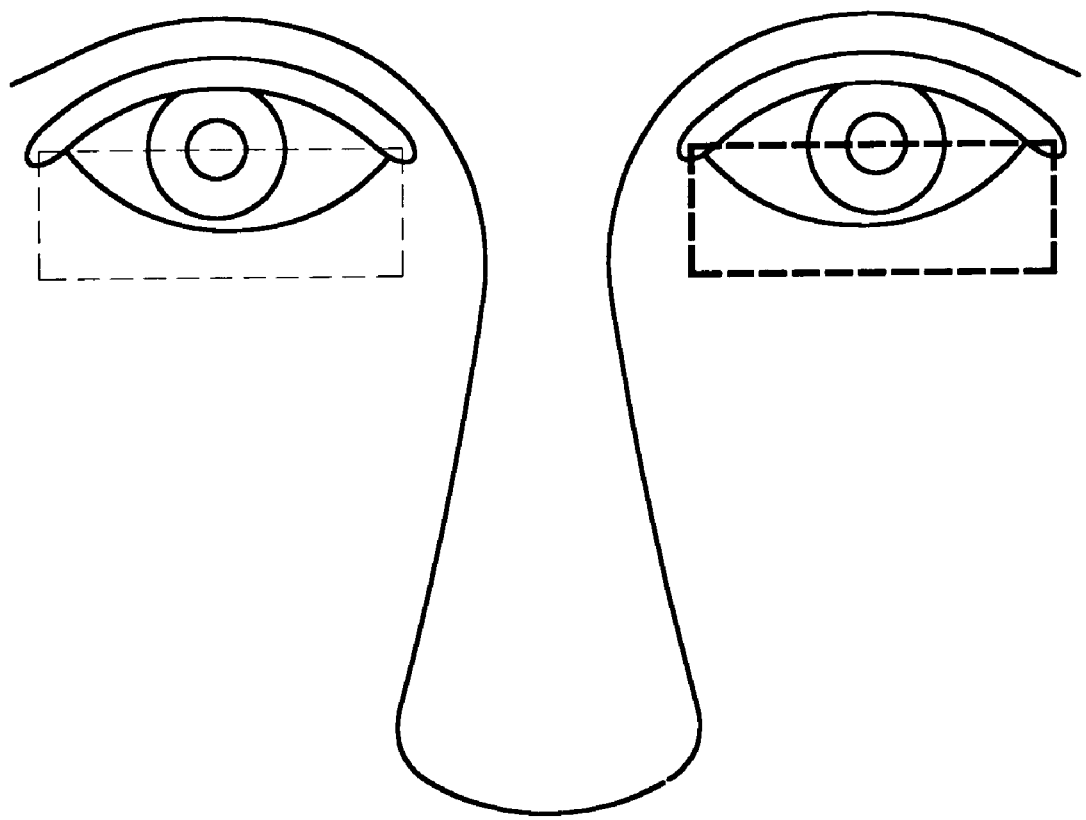
FIG. 2 shows the observed and measured portion of the eye(s), indicated with the dashed lines.
Figure 3A:
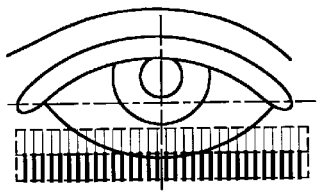
FIGS. 3A–3C shows vertical eye movement measurement. The lighter shading indicates the sensor(s) receiving more light reflection when the eye's corneal bulge moves closer to the sensor(s).
Figure 3B:
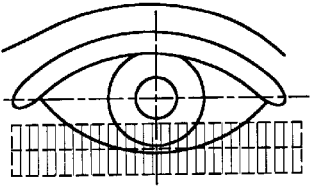
Figure 3C:
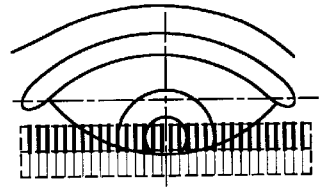
Figure 4A:
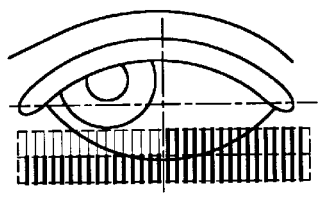
FIG. 4A shows the measurement technique for off axis measurement as the eye looks right and upward.
Figure 4B:
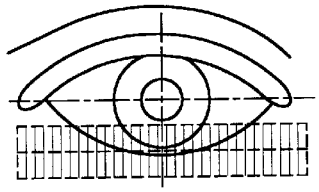
FIG. 4B shows the eye looking forward.
Figure 4C:
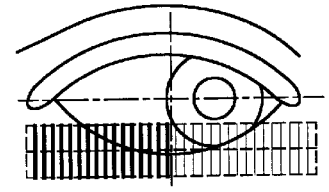
FIG. 4C shows the eye looking to its left.

The measuring technology of the preferred embodiment is comprised of infrared illuminators and sensors (e.g., photo detectors) FIGS. 1A and 1B mounted on a light weight horizontal component FIGS. 1A and 1B. The illuminators and sensors are aligned in an approximately linear fashion FIG. 1A to provide for maximum measurement range of horizontal and vertical eye movement FIGS. 2, 3A–C, and 4A–C. The horizontal component is attached to the nose bridge and extends outward under the eyes, thereby only obstructing the lower portion of the user's field of view FIGS. 1A and 1B.

The preferred version of the device employs centrally positioned illuminators with sensors above and below the illuminators FIGS. 1A and 1B. Therefore, utilizing linear or approximately linear arrays of illuminators and photo detectors FIGS. 1A and 1B, horizontal and vertical eye movement can be measured FIGS. 3A–C and 4A–C. The attached calculation technology is capable of producing data for each eye separately, or each axis separately FIGS. 3A–C and 4A–C, as well as simultaneous measurement FIG. 4A.

The measurement principle is based on the sensing of reflected light FIG. 1B, then employing robust algorithms for analysis of the measurements sensed. More light is reflected by the corneal bulge (the spherical cornea protruding from the eye) than the eye sphere itself. FIGS. 3A–C and 4A–C. For example, as the eye moves up and to its right FIG. 4A, the lesser light reflection of the eye sphere and the greater light reflection of the corneal bulge is detected by the sensors of the device.

The proprietary design for all embodiments and versions requires minimal adjustment and alignment. For accurate measurement, the device needs only to be placed on the user's nose, then balanced for the user's eye and facial features. The device itself does not require adjustment or alignment. Robust algorithms compensate for minor misalignment.

In the preferred embodiment, and all other versions, only the lower portion of the user's field of view is obstructed by the device FIGS. 1A and 1B. The horizontal component FIGS. 1A and 1B is made of a lightweight material and suitably minimized to house the necessary illuminating, sensing, and calculation means. With the horizontal component extending from the nose bridge and located approximately just above the user's cheeks and below the imaginary horizontal line passing through the center of the eye FIGS. 1A and 1B, the user has unobstructed forward, side-to-side, and upward vision. Therefore, only the lower portion of the user's downward vision is obstructed FIGS. 1A and 1B. The nose bridge causes no more obstruction of the user's visual range than the user's own nose. Thus, this device allows for a greater field of vision than the prior art, and makes this device more useful for a greater range of applications and tests.

The preferred embodiment utilizes external power and data transmission cables. Alternatively, as the device requires minimal power, it can stand alone with a small battery and wireless transmission means without affecting its measuring accuracy or minimal adjustment and vision obstruction qualities.

Other preferred embodiments may utilize a head strap or temple arms, thus widening the applicability and testing range of the device. An adjustable head strap can be attached to the top of the nose bridge piece to secure the device to the user's face and aid in adjustment and alignment. Likewise, adjustable temple arms can be attached to the nose bridge piece and secure the device to the user's face and aid in adjustment and alignment. These versions allow for rapid head movement tests, a greater range of stability tests, as well as allowing for greater accuracy during normal condition tests.

The device's measuring capabilities, minimal adjustment requirements, minimal view obstruction design, and proprietary low cost and compact design cause it to have advantages, capabilities, qualities, and usefulness not contemplated by the prior art.

B. Applications

The presently disclosed device is capable of measuring horizontal and vertical eye movement using infrared technology with only minimal restriction of the user's testable field of view and movement FIG. 1. Further, the low cost design allows greater usefulness via easier access to the device by practitioners, professionals, and researchers. Therefore, the device's uses range from communications to entertainment, and from medical to military applications.

The proprietary simplicity of the design allows the device to be applied in controlled environments, as well as field environments. The following list of applications is not intended to be exclusive, it is only a broad overview of uses. The broad capabilities of the device include testing for balance, neurological disorders, drug efficacy, testing for drug use (e.g., alcohol), or determining the consciousness or point of gaze for targeting or control and communications interaction of a pilot or driver. The device can be used on adults, children, or infants with minimal modifications and without any harm to the measuring or design qualities. Other benefits from this device are due to its low cost and wide applicability. Practitioners, professionals, and researchers will be able to perform a greater sampling of tests because of the greater quantities attainable, the light weight and comfort, and the greater field of vision offered by this device. Subjects ranging from infants to the elderly can be tested in lab environments, such as nuclear magnetic resonance testing, or it can be worn while performing normal daily functions.

Thus, based on the device's proprietary design which allows for a wide field of vision, minimal adjustment and alignment needs, and the device's light weight comfort, it is only limited by the available measuring technology and the foreseeable uses.

What is claimed is:

1. A device capable of measuring horizontal and vertical movement of a user's eye(s) independently and jointly comprising, an approximately linear oriented illuminator and sensor arrangement disposed along the horizontal axis of the user's eye(s) and comprising a) photo detectors positioned along the axis of the illuminator placement;

b) face mounting means including a nose bridge and a horizontal component housing the illuminator and sensor arrangement, said horizontal component, illuminator and sensor arrangement located in a mounted condition under the eye so as to restrict only the lower half of the visual field, leaving the forward, side to side, upward portions of the user's visual field unobstructed;

c) calculation means operatively connected to said sensor and utilizing robust algorithms, whereby said illuminator and sensor arrangement do not require precise alignment with the vertical symmetry axis of the eye(s) or precise horizontal alignment to perform accurate measurements.

* * * * *